US012714776B2

(12) United States Patent
Kibbel et al.

(10) Patent No.: US 12,714,776 B2
(45) Date of Patent: Aug. 25, 2026

(54) OPHTHALMIC SURGICAL CARTRIDGE

(71) Applicant: Carl Zeiss Meditec AG, Jena (DE)

(72) Inventors: Steffen Kibbel, Lauchheim (DE); Andreas Werner, Aalen (DE); Rupert Demleitner, Heidenheim (DE); Peter Eichert, Bissingen (DE); David Ruprecht, Urbach (DE)

(73) Assignee: Carl Zeiss Meditec AG, Jena (DE)

(*) Notice: Subject to any disclaimer, the term of this patent is extended or adjusted under 35 U.S.C. 154(b) by 1010 days.

(21) Appl. No.: 17/949,053

(22) Filed: Sep. 20, 2022

(65) Prior Publication Data

US 2023/0086784 A1 Mar. 23, 2023

(30) Foreign Application Priority Data

Sep. 21, 2021 (DE) .................... 10 2021 210 482.7

(51) Int. Cl.
*A61M 1/00* (2006.01)
*A61F 9/007* (2006.01)

(52) U.S. Cl.
CPC ......... *A61M 1/772* (2021.05); *A61F 9/00781* (2013.01)

(58) Field of Classification Search
CPC .......... A61M 1/772; A61M 1/73; A61M 1/82; A61M 1/77; A61M 2210/0612; A61M 3/0201; A61M 3/0202; A61M 3/0254; A61F 9/00781; A61F 9/00736; A61F 2/16
See application file for complete search history.

(56) References Cited

U.S. PATENT DOCUMENTS

| | | | |
|---|---|---|---|
| 4,775,470 A | 10/1988 | Zook | |
| 10,722,619 B2 | 7/2020 | Kuebler et al. | |
| 2008/0062384 A1* | 3/2008 | Rombach | A61B 3/103 351/211 |

FOREIGN PATENT DOCUMENTS

| | | |
|---|---|---|
| DE | 3716765 A1 | 11/1987 |
| DE | 102016201297 B3 | 3/2017 |

OTHER PUBLICATIONS

Office Action issued in German Patent Application No. DE 10 2021 210 482.7, dated May 24, 2022 (from which this application claims priority) and English language translation thereof.

* cited by examiner

*Primary Examiner* — Dung T Ulsh
(74) *Attorney, Agent, or Firm* — Ewers IP Law PLLC; Falk Ewers

(57) ABSTRACT

An ophthalmic surgical cartridge has a fluid pump with a pump chamber and a drive chamber which are separated by a fluid-tight and ion-tight partition element. A body fluid is suppliable to the pump chamber and a drive fluid is suppliable to the drive chamber. A deformation or change in position of a portion of the partition element is achievable with the drive fluid which increases the second volume in size and decreases the first volume in size to drain the body fluid from the pump chamber. The drive chamber has a front side wall with an edge zone in which only a single passage opening is provided, through which the drive fluid is suppliable into the drive chamber to fill the drive chamber with the drive fluid, and through which said drive fluid can be drained from the drive chamber to remove the drive fluid from the drive chamber.

7 Claims, 2 Drawing Sheets

OPHTHALMIC SURGICAL CARTRIDGE

CROSS REFERENCE TO RELATED APPLICATIONS

This application claims priority to German patent application DE 10 2021 210 482.7, filed Sep. 21, 2021, the entire content of which is incorporated herein by reference.

TECHNICAL FIELD

The disclosure relates to an ophthalmic surgical cartridge.

BACKGROUND

There are a number of surgical techniques for treating clouding of the crystalline lens, which is referred to in medicine as a cataract. The most widespread technique is phacoemulsification, in which a thin hollow needle is introduced into the crystalline lens and is induced to make ultrasonic vibrations. In its immediate surroundings, the vibrating hollow needle comminutes the lens in such a way that many small lens particles arise, which can be aspirated through a line with a pump. A flushing fluid (irrigation fluid) is fed during this process, with the aspiration of the lens particles with the fluid, referred to together as aspiration fluid, taking place through an aspiration line. The irrigation fluid, which is lead to a body to be treated, and the aspiration fluid, which is drained from the body to be treated, are referred to as body fluid below. When the lens has been completely emulsified and removed, a new artificial lens can be inserted into the empty capsular bag, and so a patient treated in this way can recover good vision.

Both irrigation fluid and aspiration fluid can be conveyed with a pump. This can be carried out using a peristaltic pump in each case, but pressure variations that are disadvantageous for the stability of the intraocular pressure may occur. Irrigation fluid or aspiration fluid can also be conveyed with a membrane pump. In this case, it is possible to convey the body fluids with low pressure variations but a drive fluid at a relatively high pressure must be supplied for operating the membrane pump and, in particular, for driving a membrane movement. To obtain high reliability, this requires a robust structure that can be subjected to significant mechanical loads, with only small dimensional deviations being tolerable.

SUMMARY

It is therefore an object of the disclosure to provide an ophthalmic surgical cartridge which may have a less robust design but is nevertheless reliably usable.

The object is achieved by an ophthalmic surgical cartridge as described herein.

The ophthalmic surgical cartridge according to an aspect of the disclosure has a fluid pump which has at least one pump chamber with a first volume and a drive chamber with a second volume that is separated from said pump chamber by a fluid-tight and ion-tight partition element, the partition element having a partition element center axis, the partition element being connected by way of its edge to the fluid pump such that the partition element and its edge are not displaceable in a direction running parallel to the partition element center axis. A body fluid is suppliable to the pump chamber through a body fluid feed line, the body fluid being an irrigation fluid or an aspiration fluid, and a drive fluid that differs from the body fluid is suppliable to the drive chamber, a deformation or change in position of at least a portion of the partition element being achievable by way of said drive fluid, as a result of which the second volume can be made to increase in size and, at the same time, the first volume can be made to decrease in size, as a result of which the body fluid can be drained from the pump chamber through a body fluid discharge line. The drive chamber has a front side wall, with a front side wall center axis running through the geometric center of the front side wall and perpendicular to the front side wall, the front side wall center axis running in a line with the partition element center axis, with the front side wall having an edge zone in which only a single passage opening is provided, through which the drive fluid is suppliable into the drive chamber from outside of the drive chamber in order to fill the drive chamber with the drive fluid, and through which said drive fluid can be drained from the drive chamber in order to remove the drive fluid from the drive chamber.

The passage opening is arranged in an edge zone of the front side wall of the drive chamber, i.e., not along the front side wall center axis and hence off centered. A pump chamber is mechanically more stable in an edge zone than in a central zone of a drive chamber of a pump chamber which has a partition element. The larger mechanical stability in an edge zone of the front side wall of a pump chamber is advantageous since the drive fluid, such as air for example, must be supplied in very well sealed fashion to the drive chamber so that a reliable deformation or change in position of the partition element is achievable. However, good sealing requires a high contact force of a drive fluid feed element on the front side wall of the drive chamber. Consequently, a high contact force can be applied to the front side wall in the cartridge according to an aspect of the disclosure, without this leading to a significant deformation of the front side wall, with the front side wall needing to be dimensioned less robustly and strongly than previously. Hence, a lightweight design without reinforcing ribs and the like is possible, with it nevertheless being possible to achieve reliable sealing and hence a reliable control of the deformation or change in position of the partition element and hence pumping of a body fluid. Since only a single passage opening is provided, it is also only a single seal that needs to reliably seal; this is easily implementable from a technical point of view and does not lead to larger complexity in the structure. A lightweight design is particularly desirable since the cartridge according to an aspect of the disclosure is a consumable which, for reasons of sterility, is only used once and has to be disposed of as waste following the operation. The amount of waste can be reduced as a result of a lightweight design structure, which is desirable for ecological reasons.

A very asymmetric structure of the cartridge is present as a result of arranging the passage opening in an edge zone of the front side wall of the drive chamber. Consequently, the drive fluid flows into the drive chamber from an edge and is then distributed within the drive chamber. The inventors have discovered that the partition element deforms or is displaced along the partition element center axis when the drive chamber is filled with drive fluid or when drive fluid is removed from the drive chamber, despite this asymmetric structure of the cartridge, and that uniform pumping of a body fluid is achieved.

According to an exemplary embodiment, a distance from the front side wall center axis to an inner edge of the edge zone is at least 70% of the distance from the front side wall center axis to an outer edge of the edge zone. This ensures that a high mechanical stability of the drive chamber in the region of the edge zone can be used.

Typically, an edge region is provided around the passage opening as a planar sealing surface on the front side wall of the drive chamber. This is advantageous as this allows a good seat of a seal for the drive fluid feed element such that there is no risk of leakiness in the case of a high pressure of the drive fluid.

According to a further exemplary embodiment of the disclosure, a drive chamber peripheral wall can run around the front side wall center axis and the edge region can reach up to the drive chamber peripheral wall as a sealing surface. A contact force of the drive fluid feed element acting on the sealing surface can therefore at least partly press on the end side of the drive chamber peripheral wall, as a result of which very little bending arises on the front side wall and very good sealing is rendered possible.

Typically, the edge region has an area of up to 50 $mm^2$ and the passage opening has a cross-sectional area of up to 20 $mm^2$. This means that a relatively small contact area is provided for sealing a drive fluid feed element and hence said contact area can be placed in a region of the edge zone far away from the front side wall center axis such that there is little deformation of the front side wall.

The second volume of the drive chamber can have a size of 1 to 20 $cm^3$. As a result, the drive chamber might not need to be refilled so frequently during an ophthalmic surgical operation, and so fluidic and acoustic disturbances possible during filling/emptying of the drive chamber only occur minimally.

The partition element may have a partition element center axis that runs perpendicular to the partition element surface. Typically, the partition element has a larger moment of inertia in a first region around the partition element center axis than in a second region at an edge of the partition element situated within the drive chamber. This is advantageous since, e.g., a metal element may be provided in the first region, it being possible to detect said metal element by a sensor arranged outside of the drive chamber. Hence, a position of the partition element in the first region is easily detectable.

The disclosure also relates to a panel which has a cartridge accommodation region for accommodating an ophthalmic surgical cartridge according to any one of the aforementioned exemplary embodiments. Additionally, the panel has a drive fluid feed element, which is configured to feed drive fluid into the drive chamber of the fluid pump. The panel additionally has a control unit for controlling the drive fluid feed element. Optionally, the panel has a sensor which allows a position of the partition element to be captured in a portion around the partition element center axis.

BRIEF DESCRIPTION OF THE DRAWINGS

The disclosure will now be described with reference to the drawings wherein.

DESCRIPTION OF EXEMPLARY EMBODIMENTS

Figure 1:
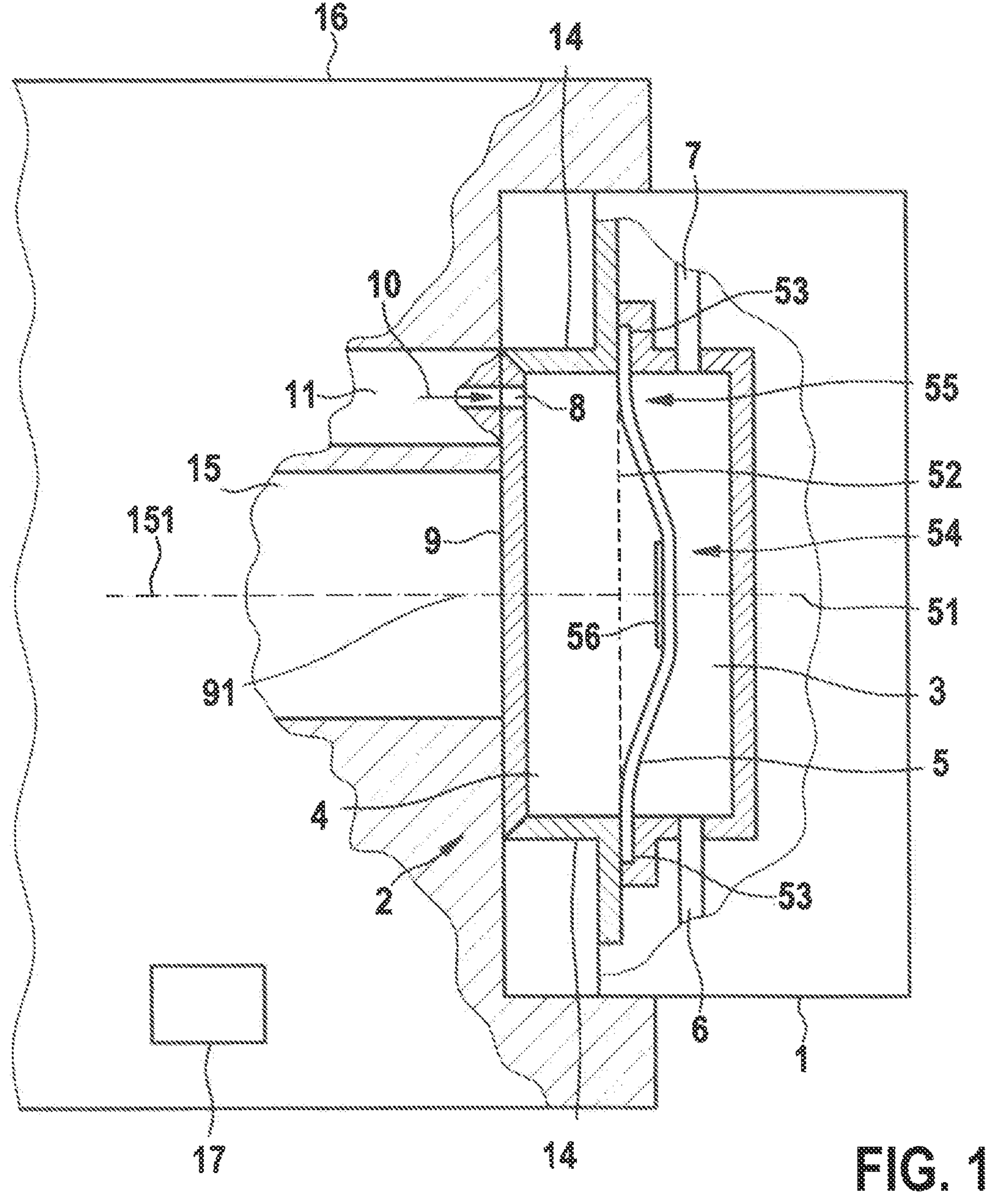
FIG. 1 shows a schematic illustration of the cartridge in a side view according to an exemplary embodiment of the disclosure.

FIG. 1 shows a partial sectional illustration of a side view of an ophthalmic surgical cartridge 1. The cartridge 1 includes a fluid pump 2 which has a pump chamber 3 with a first volume and a drive chamber 4 with a second volume. The pump chamber 3 is separated from the drive chamber 4 by a partition element 5, which, by way of its edge 53, is connected to the fluid pump 2 between the drive chamber 4 and the pump chamber 3. By way of its edge 53, the partition element 5 is connected to the drive chamber 4 and the pump chamber 3 such that, at its edge 53, it is not displaceable in an axial direction running parallel to a partition element center axis 51. It is typically securely clamped at its edge 53. However, away from the edge 53, the partition element 5 may be deformable or displaceable in terms of its position in the axial direction. The partition element 5 can be a membrane, a diaphragm, or a film. The partition element 5 is typically formed from an elastic plastic as it can then be deformed with little expenditure of force. However, it may also be formed from a substance that is not a plastic, for example from a metallic substance. It is possible that the partition element 5 is formed from a single substance or a composite.

The pump chamber 3 additionally includes a body fluid feed line 6, through which a body fluid such as an irrigation fluid or an aspiration fluid, for example, can be fed to the pump chamber 3. Moreover, the pump chamber 3 includes a body fluid discharge line 7, through which the body fluid contained in the pump chamber can be removed.

The partition element 5 includes a partition element center axis 51 and a partition element rest plane 52. The partition element rest plane 52 is a plane that typically runs through the edge 53 of the partition element that is coupled to the pump chamber 3 and the drive chamber 4. The partition element center axis 51 runs perpendicular to the partition element rest plane 52 and through the geometric center of the partition element 5. In a portion along the center axis 51, the partition element 5 can carry out a change in its position or deflection by virtue of, for example, deforming or displacing from the partition element rest plane 52 to the left-hand side or in the direction to the right-hand side as shown in FIG. 1, that is to say along the partition element center axis 51. If the partition element 5 is in a position to the left of the partition element rest plane 52, a body fluid is contained in the pump chamber 3 and a valve on the body fluid feed line 6 is closed, with a valve on the body fluid discharge line 7 being open, then the body fluid can be removed from the pump chamber 3 by way of a deformation or displacement of the partition element 5 in the direction of the right-hand side of the partition element rest plane 52. The second volume of the drive chamber 4 increases in size while the first volume of the pump chamber 3 reduces at the same time. This procedure is reversible. This means that when a valve on the body fluid discharge line 7 is closed and a valve on the body fluid feed line 6 is open, a body fluid can be fed to the pump chamber 3 or sucked into the pump chamber 3 as a result of negative pressure due to a deformation or displacement of the partition element 5 in the direction to the left of the partition element rest plane 52. In this case, there is a reduction in the second volume while the first volume increases at the same time. In this way, body fluid can be pumped into the pump chamber 3 or pumped out of the pump chamber 3.

Figure 2:
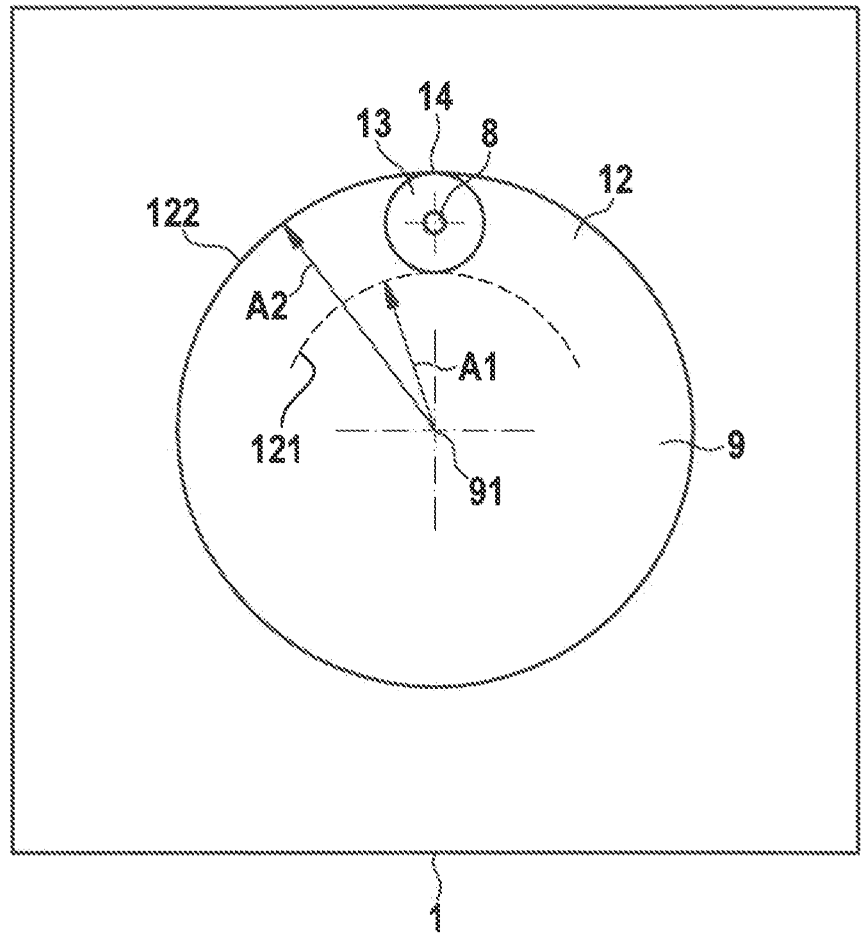
FIG. 2 shows a schematic illustration a front view of the cartridge shown in FIG. 1.

The described deformation of the partition element 5 may be caused by a drive fluid, see arrow 10, the drive fluid being suppliable to the drive chamber 4 through a passage opening 8 in a front side wall 9 of the drive chamber 4 with a drive fluid feed element 11. As is evident from FIG. 2, the front side wall 9 has an edge zone 12, in which the passage opening 8 is provided. The front side wall 9 has a front side wall center axis 91, which runs perpendicular to the front side wall 9 and through the geometric center of the front side wall 9. In this case, the edge zone 12 can be defined such that a distance A1 from the center axis 91 to an inner edge 121 of the edge zone 12 is at least 70%, typically 80%, and particularly typically 90% of a distance A2 from the center axis 91 to an outer edge 122 of the edge zone 12.

So that the drive fluid 10 reaches the drive chamber 4 without fluid loss, an edge region 13 is provided on the front side wall 9 in the edge zone 12, said edge region being provided around the passage opening 8 as a planar sealing surface. There, the drive fluid feed element 11 can be brought into secure and reliable contact with the edge region 13 with a seal. As is evident from FIG. 1, the drive chamber 4 has a drive chamber peripheral wall 14, which runs around the center axis 91 of the front side wall 9. In the exemplary embodiment shown, the edge region 13 is arranged such that it reaches up to the drive chamber peripheral wall 14. Should the drive fluid feed element 11 be arranged in the edge region 13, the contact force exerted by the feed element 11 on the drive chamber 4 can be partly absorbed by the drive chamber peripheral wall 14. The risk of the front side 9 of the drive chamber 4 bending on account of the high contact force of the drive fluid feed element 11 and the drive fluid 10 reaching the drive chamber 4 in no longer fully sealed fashion, i.e., the risk of a leak of the drive fluid being present, is very low or practically not present. Hence, both the drive chamber peripheral wall 14 and the front side wall 9 can be constructed to be relatively thin and in a lightweight design. Hence, no large material strength and robust structure is required despite the high contact force, but a high reliability for the operation of the pump chamber 3 is achievable.

In a development of the disclosure, the partition element 5 has a larger moment of inertia in a first region 54 around the partition element center axis 51 than in a second region 55 at the edge 53 of the partition element 5. The larger moment of inertia can be achieved by virtue of the partition element 5, in the first region 54 around the partition element center axis 51, having at least one metal element 56 with a larger modulus of elasticity in tension than the partition element 5. The metal element 56 can be used to detect the position of the partition element 5 with a position sensor 15 based for example on inductive or capacitive principles. The position sensor 15 may have a center axis 151 which corresponds to the center axis 51 of the partition element 5. This is advantageous since arranging the passage opening 8 in the edge zone 13 makes a central region of the front side wall 9 available for the placement of the position sensor 15 close to the front side wall 9 and hence this central region can easily be used.

The at least one metal element 56 can be coupled to the partition element 5. The at least one metal element 56 can also be integrated in the partition element 5 or be enveloped by the partition element 5.

The partition element center axis 51 runs in a line with the front side wall center axis 91. Typically, the partition element center axis 51 and the front side wall center axis 91 and the center axis 151 of the position sensor 15 run in one line.

The position sensor 15 and the drive fluid feed element 11 can be provided in a panel 16. The position sensor 15 can be in contact with the front side wall 9 or be arranged at a distance therefrom. The panel 16 is configured to securely accommodate the cartridge 1 in a cartridge accommodation region. The panel 16 comprises a control unit 17 provided to control the drive fluid feed element 11, the position sensor 15 and a volumetric flow rate and/or pressure of body fluid in the cartridge 1. The cartridge 1 can have a plurality of pump chambers 3.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Ophthalmic surgical cartridge
2 Fluid pump
3 Pump chamber
4 Drive chamber
5 Partition element
6 Body fluid feed line
7 Body fluid discharge line
8 Passage opening
9 Front side wall
10 Drive fluid
11 Drive fluid feed element
12 Edge zone
13 Edge region
14 Drive chamber peripheral wall
15 Position sensor
16 Panel
17 Control unit
51 Partition element center axis
52 Partition element rest plane
53 Edge of the partition element
54 First partition element region
55 Second partition element region
56 Metal component part
91 Front side wall center axis
121 Inner edge of the edge zone 12
122 Outer edge of the edge zone 12
151 Center axis of the position sensor 15

What is claimed is:

1. An ophthalmic surgical cartridge, comprising:

at least one fluid pump having a pump chamber, a drive chamber, and a fluid-tight and ion-tight partition element with an edge, wherein the pump chamber defines a first volume and the drive chamber defines a second volume, wherein the drive chamber is separated from the pump chamber by the fluid-tight and ion-tight partition element, wherein the fluid-tight and ion-tight partition element defines a partition element center axis, wherein the fluid-tight and ion-tight partition element is connected on the edge to the at least one fluid pump such that the fluid-tight and ion-tight partition element and the edge are not displaceable in a direction running parallel to the partition element center axis, wherein a body fluid is suppliable to the pump chamber through a body fluid feed line, the body fluid being an irrigation fluid or an aspiration fluid, wherein a drive fluid that differs from the body fluid is suppliable to the drive chamber, a deformation or change in position of at least a portion of the fluid-tight and ion-tight partition element being achievable with the drive fluid, as a result of which the second volume can be made to increase in size and, at the same time, the first volume can be made to decrease in size, as a result of which the body fluid can be drained from the pump chamber through a body fluid discharge line, wherein the drive chamber has a front side wall defining a front side wall center axis running through a geometric center of the front side wall and perpendicular to the front side wall, the front side wall center axis running in a line with the partition element center axis, and wherein the front side wall has an edge zone in which only a single passage opening is provided, through which the drive fluid is suppliable into the drive chamber from outside of the drive chamber to fill the drive chamber with the drive fluid, and through which the drive fluid can be drained from the drive chamber to remove the drive fluid from the drive chamber.

2. The ophthalmic surgical cartridge as claimed in claim 1, wherein a distance from the front side wall center axis to an inner edge of the edge zone is at least 70% of the distance from the front side wall center axis to an outer edge of the edge zone.

3. The ophthalmic surgical cartridge as claimed in claim 1, wherein an edge region is provided around the passage opening as a planar sealing surface on the front side wall of the drive chamber.

4. The ophthalmic surgical cartridge as claimed in claim 3, wherein a drive chamber peripheral wall runs around the front side wall center axis and the edge region reaches up to the drive chamber peripheral wall as a sealing surface.

5. The ophthalmic surgical cartridge as claimed in claim 3, wherein the edge region has an area of up to 50 $mm^2$ and the passage opening has a cross-sectional area of up to 20 $mm^2$.

6. The ophthalmic surgical cartridge as claimed in claim 1, wherein the second volume has a size of 1 to 20 $cm^3$.

7. The ophthalmic surgical cartridge as claimed in claim 1, wherein the fluid-tight and ion-tight partition element has a larger moment of inertia in a first region around the partition element center axis than in a second region at an edge of the fluid-tight and ion-tight partition element located within the drive chamber.

* * * * *